United States Patent [19]

Nakahara et al.

[11] Patent Number: 5,305,366
[45] Date of Patent: Apr. 19, 1994

[54] THIN FILM FORMING APPARATUS

[75] Inventors: Takehiko Nakahara; Masao Koshinaka; Nobuyuki Kosaka; Toshimasa Tomoda, all of Hyogo, Japan

[73] Assignee: Mitsubishi Denki Kabushiki Kaisha, Tokyo, Japan

[21] Appl. No.: 817,660

[22] Filed: Jan. 7, 1992

[30] Foreign Application Priority Data

Jan. 9, 1991 [JP] Japan .................................. 3-011677
Mar. 26, 1991 [JP] Japan .................................. 3-084516

[51] Int. Cl.$^5$ ........................................... G01N 23/223
[52] U.S. Cl. ............................. 378/45; 378/49; 378/83
[58] Field of Search ....................... 378/45-49, 378/82, 83, 84, 85

[56] References Cited

U.S. PATENT DOCUMENTS

| 3,663,812 | 5/1972 | Koenig . | |
|---|---|---|---|
| 4,169,228 | 9/1979 | Briska et al. | 378/45 |
| 4,256,961 | 3/1981 | Shoji et al. | 378/49 |
| 4,271,353 | 6/1981 | Ohtsuki et al. | 378/83 |

FOREIGN PATENT DOCUMENTS

| 62-214335 | 9/1987 | Japan | 378/45 |
|---|---|---|---|
| 2-93355 | 4/1990 | Japan | 378/45 |
| 2204066 | 11/1988 | United Kingdom . | |

OTHER PUBLICATIONS

"Chemical Analyses of Surfaces by Total Reflection Angle X-Ray Spectroscopy in RHEED Experiments" Hasegawa et al., Journal of Applied Physics, vol. 24, No. 6, Jun. 1985, pp. L387-L390.
Knoth & Schwenke "A New Totally Reflecting X-Ray Fluorescence Spectrometer w/Detection Limits" below 10-11 g, Institut fur Physi.

Primary Examiner—Craig E. Church
Attorney, Agent, or Firm—Wolf, Greenfield & Sacks

[57] ABSTRACT

This invention relates to a method and apparatus for analyzing a plurality of elements that are present on the surface of a material of interest or in its neighborhood, as well as a thin-film forming apparatus that is capable of measuring the composition of a sample during thin film formation in the process of semi-conductor fabrication. The apparatus are characterized in that a detector is isolated from the light and heat generated in a sample making mechanism by means of a shield which is not only heat-resistant but also transmissive of fluorescent X-ray containing soft X-rays of 1 Kev and below and that a mirror for total reflection of X-rays which is equipped with slits capable of adjusting the incident and exit angles of fluorescent X-rays from the sample excited with an excitation source as well as the ranges of those angles is provided either at the entrance or exit of said shield or at both.

38 Claims, 16 Drawing Sheets

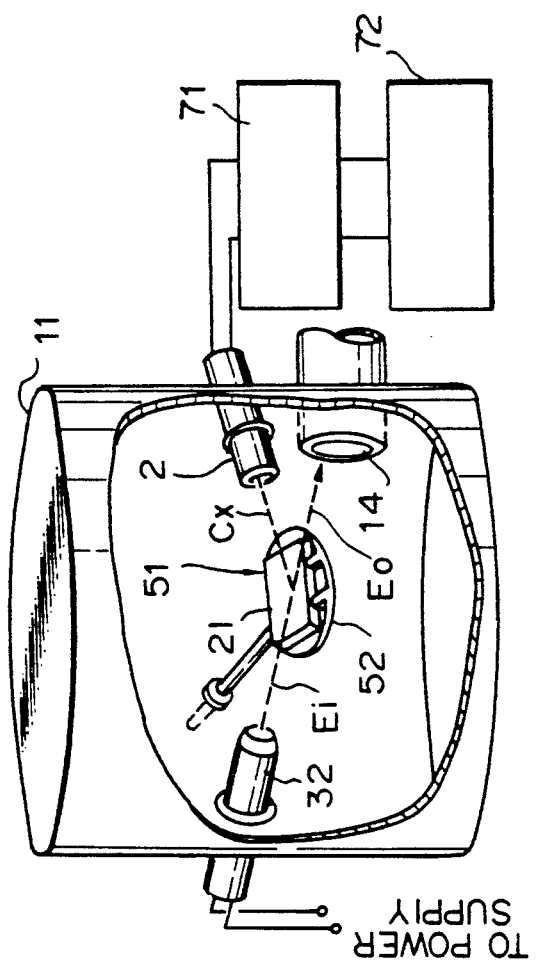

THIN FILM FORMING APPARATUS

BACKGROUND OF THE INVENTION

This invention relates to a thin-film forming apparatus for use in the fabrication of electronic devices, semiconductors, etc. More particularly, this invention relates to a thin-film forming apparatus that is capable of consecutively measuring the composition of a sample in the process of forming the desired thin film on the sample. This invention also relates to a method and apparatus for analyzing a plurality of elements that are present on the surface of a material of interest or in its neighborhood, as well as a thin-film forming apparatus that is capable of measuring the composition of a sample during thin film formation in the process of semi-conductor fabrication.

As the scale of integration of electronic devices, semiconductor devices, etc. has increased while their feature size has decreased today, it has become apparent that the performance of those devices tends to depend on the quality of the thin films they use. For example, if the silicon (Si) to oxygen (O) ratio in a silicon dioxide ($SiO_2$) deviates from the stoichiometric value of 1:2, one may conclude that an unwanted substance other than $SiO_2$ has entered the film to change its dielectric constant, whereby desired high-frequency characteristics cannot be attained. Further, when forming a thin compound film, it is often difficult to attain the desired composition primarily due to the differences in sputtering yield and sticking coefficient. Conventionally, a composition analyzer is used to evaluate the composition of a thin film after making it with a thin-film forming apparatus. But, in this case, it has been difficult to form the thin film without any change in its composition due to variations in the process conditions being properly corrected during thin film formation. Under these circumstances, attempts have been made to consecutively measure the change that will occur in the composition of the thin film being formed.

FIGS. 17 and 18 are diagrammatic views of the prior art thin-film forming apparatus that is described in Ino et al., "Surface Analysis by RHEED Excited Total Reflection Angular X-Ray Spectroscopy (TRAXS)" in Oyo Butsuri (Applied Physics), 56, 7, 1987, pp. 843-850. FIG. 17 shows the apparatus as it is equipped with an elemental analyzer for measuring the compositional changes of a sample. Shown by 1 is a vessel for keeping an X-ray detector in vacuum; 3 is a window that maintains the vacuum enclosure of the X-ray detector but which admits the passage of X-rays; 6 is a liquid nitrogen dewar vessel for cooling the X-ray detector; 7 is an X-ray transmitting window; 10 is a thin-film forming vacuum chamber; 12 is a sample making mechanism; 13 is an exhaust unit for degasifying the vacuum chamber 10; 21 is a sample; and 31 is an excitation source that excites the elements in the sample 21 to emit their characteristic X-rays (fluorescent X-rays). Shown by 51 is a sample holder with a stage 52 for mounting the sample 21 in position.

FIG. 18 shows the interior of the vessel 1 in detail. Shown by 2 is the X-ray detector (hereunder sometimes referred to simply as the "detector"); 4 is an amplifier for amplifying the output signal from the detector 2; and 5 is a rod that guides the signal from the amplifier 5 to the outside of the vacuum enclosure and which lets in a cooling medium for cooling the detector.

The operation of the apparatus shown in FIGS. 17 and 18 is described below. To form a thin film of gallium arsenic (GaAs), he activates the mechanism 12 is activated to have gallium (Ga) and arsenic (As) evaporated onto the sample 21. During the thin-film formation, an excitation beam such as an electron beam generated from the excitation source 31 such as an electron gun is incident upon the sample 21, whereby Ga and As are excited to emit their characteristic X-rays. The emitted X-rays exit from the chamber 10 through the window 7 and travel in air atmosphere to be admitted into the detector 2 through the window 3 at the front of the vessel 1. Signals associated with the detected characteristic X-rays are amplified by the amplifier 4 and the amplified signals pass through the rod 5 to be fed into a spectrum analyzer (not shown) or some other suitable external circuit. With this arrangement, the composition of the surface of sample 21 can be analyzed while a thin film is formed on the sample.

The prior art elemental analyzer is described below in detail. FIG. 19 is a diagrammatic view of the elemental analyzer described in Japanese Patent Public Disclosure No. 82840/1985. As shown, the analyzer comprises the detector 2, a vacuum chamber 11, an exhaust port 14 which is connected to a vacuum pump (not shown) that is operated to keep the inside of the chamber 11 in vacuum, an electron gun 32 for emitting an electron beam onto the sample 21, the sample holder 51, the sample mounting stage 52, a spectrum analyzer 71 for spectrum separating the X-rays detected with the detector 2, and a memory unit 72 for storing the output of the spectrum analyzer. The memory unit 72 may be replaced by a display unit.

The operation of the elemental analyzer shown in FIG. 19 is described below. The sample 21 is to be mounted on the stage 52 at the distal end of the sample holder 51. In order to facilitate its mounting, an opening/closing portion is provided in a suitable area of the vacuum chamber 11 so that the sample 21 can be pushed into the chamber 11 via said portion. Alternatively, the vessel 11 may be so constructed that the sample holder 51 can be pulled out for mounting the sample 21 outside the vessel. The sample holder 51 is equipped with bellows or some other suitable means for permitting it to rotate or move back and forth so that the position and inclination of the sample 21 can be freely adjusted.

In response to a current from a power source, the electron gun 32 generates and emits an electron beam. The emitted electron beam is focused by an optional electronic lens and a collimator (not shown) to be incident on the surface of the sample 21. This electron beam excites the elements that are present on the surface of the sample 21 and in its neighborhood, whereby X-rays characteristic of the excited elements are emitted for detection with the detector 2. The detected X-rays are spectrum separated with the spectrum analyzer 71 and the X-ray spectra supplied from the spectrum analyzer 71 are stored in the memory unit 72.

The angle at which emitted X-rays are picked up is selected at the angle of total reflection of electromagnetic waves (generally characteristic X-rays) emitted from the sample 21, namely the critical angle, or at nearby angles. The reason for selecting the critical angle as the angle at which emitted X-rays are to be picked up is described below on the basis of the disclosures in "Oyo Butsuri (Applied Physics)", 56, 7, 1987, pp. 842-850 and "Japanese Journal of Applied Physics", 24, 6, 1985, pL. 387-390. In the following discussion, each of the angles such as the critical angle and glancing angle is measured as the angle the incident or emerging X-ray forms with the surface of the sample.

FIG. 20 shows how X-rays leaving the surface of a material to enter vacuum are refracted. As shown, the intensity of such X-rays decreases sharply if they are emitted at smaller angles than a certain critical value $\theta_c$. The value of $\theta_c$ coincides with the critical angle for total reflection that occurs when X-rays of the same energy are launched from vacuum into the material of interest and it is expressed by:

$$\theta_c = \left( 5.4 \times 10^{10} \times \frac{Z}{A} \cdot \rho \right)^{\frac{1}{2}} \cdot \lambda \quad (1)$$

where Z, A and $\rho$ are the atomic number, mass number and density, respectively, of the material of interest, and $\lambda$ is the wavelength of the incoming and outgoing X-ray.

Take, for example, the case where an electron beam is incident on the surface of the material. The characteristic X-rays are refracted as shown in FIG. 21 and those which are picked up at angles close to the critical angle $\theta_c$ contain information from the surface layer whereas those picked up at angles greater than $\theta_c$ contain information from deeper areas. As eq. (1) shows, the critical angle $\theta_c$ varies with the wavelength of incoming and outgoing X-ray and the shorter its wavelength (hence, the higher its energy), the smaller the critical angle is. In addition, the characteristic X-rays have energy values peculiar to the associated elements. For example, the intensity of characteristic X-rays emitted from the sample 21 having approximately one atomic layer of silver (Ag) evaporated on the Si surface has a pickup angle dependency as shown in FIG. 22. The characteristic X-rays emitted by Ag can be detected with a very high sensitivity by picking them up at the angle of total reflection of Ag characteristic X-rays with respect to Si or at nearby angles. In addition, the characteristic X-rays emitted from the neighborhood of the Si surface can be selectively detected by picking up the characteristic X-rays emitted by Si at the angle of total reflection of Si characteristic X-rays with respect to Si or nearby angles.

To take another example, the intensity of characteristic X-rays emitted from the sample 21 having calcium (Ca), iron (Fe) or copper (Cu) deposited as a trace impurity on the Si surface has a pickup angle dependency as shown in FIG. 23. Obviously, the angle of total reflection of emitted characteristic X-ray with respect to Si varies with the species of element that emits the X-ray. If the sample 21 is made of zinc sulfide (ZnS), the intensity of characteristic X-rays emitted from the sample has a pickup angle dependency as shown in FIG. 24. Obviously, the angle of total reflection of the Zn characteristic X-ray with respect to ZnS differs from that of the S characteristic X-ray with respect to ZnS and at the angle of total reflection of Zn, the S characteristic X-ray has a very small intensity whereas at the angle of total reflection of S, the Zn characteristic X-ray contains more of the information from a deep area of the sample.

A problem with the prior art elemental analyzer constructed in the manner described above, is that if more than one element is present in the neighborhood of the surface of the sample 21, the different values of energy possessed by X-rays characteristic of the individual elements provide different angles of total reflection for the sample 21. As a result, if the characteristic X-ray emitted by a certain element is detected at an angle in the neighborhood of the angle of total reflection for that element, the intensity of the characteristic X-ray of another element will decrease or more of the information from a deeper area will be detected to reduce the sensitivity of measurement for the surface of the sample (i.e., more of the unwanted information will be contained in information about the surface of the sample 21).

The prior art thin-film forming apparatus capable of compositional measurement of samples, which has the construction shown in FIG. 17, has had the following disadvantages:

(1) Conventionally, the X-ray transmissive window 7 is formed of a beryllium (Be) foil which, at a sufficient thickness to keep an ordinary degree of vacuum, will absorb soft X-rays having an energy of no more than 1 keV and this has made it difficult to measure the characteristic X-rays of materials such as oxides and carbides that contain light elements;

(2) Even if the X-ray transmissive window 7 is formed of an organic material that transmits soft X-rays (e.g. Parylene), the heat of radiation that is generated from the substrate and other sources during thin film formation can potentially soften or melt the X-ray transmissive window;

(3) Even if the apparatus is so modified as to enable the measurement of light elements, the efficiency of generation of characteristic X-rays decreases drastically with the decreasing atomic number of light elements such as oxygen (O), nitrogen (N) and carbon (C). With compounds containing such light elements, the yield of characteristic X-rays will vary considerably with the species of element even if the compositional ratio of any two elements is 1:1. Accordingly, in performing pulse measurements on the characteristic X-rays entering the detector 2, the counting rate of pulses is limited by the higher of the two yields of characteristic X-rays and the counting rate for the measurement of characteristic X-rays of the lower of the two yields becomes very low. Under the circumstances, the time of pulse measurement must be prolonged in order to achieve a higher precision of measurement. Since it takes a long time to accomplish the measurement of materials containing light elements, it is difficult to catch up with the high speed of thin film formation, so has it been to consecutively measure the composition of the sample 21 in the process of thin film formation if it contains light elements.

SUMMARY OF THE INVENTION

The present invention has been accomplished under these circumstances and has as an object providing a thin-film forming apparatus that is capable of consecutively measuring the composition of a sample in the process of thin film formation even if it contains light elements.

Another object of the present invention is to provide a method of elemental analysis by which measurements can be performed on a plurality of elements present in the neighborhood of a sample surface without deteriorating the surface sensitivity for any of those elements.

A further object of the present invention is to provide an elemental analyzer that is capable of performing measurements on a plurality of elements in the manner described above.

According to one embodiment of the present invention there is provided a thin-film forming apparatus characterized in that a detector is isolated from the light and heat generated in a sample making mechanism by means of a shield that is not only heat-resistant but also transmissive of fluorescent X-rays containing soft X-rays of 1 keV and below and that a mirror for total reflection of X-rays that is equipped with slits capable of adjusting the incident and exit angles of fluorescent X-rays from the sample excited with an excitation source, as well as the ranges of those angles is provided either at the entrance or exit of said shield or at both.

According to another embodiment of the present invention there is provided a thin-film forming apparatus comprising: an excitation source that excites the elements in a sample to emit their own characteristic X-rays; a total reflecting mirror that reflects said characteristic X-rays; an X-ray detector that detects the characteristic X-rays as reflected from the total reflecting mirror; slits that determine the range of incident angles for the characteristic X-rays that are to be incident on the total reflecting mirror, as well as the range of exit angles for those characteristic X-rays which have been reflected from the total reflecting mirror and which reach said detector; and a shield that isolates the detector from light and heat and that is not only heat-resistant but also transmissive of fluorescent X-rays containing soft X-rays of 1 keV and below.

According to still another embodiment of the present invention, there is provided a method of elemental analysis that comprises: a radiation step in which energy particles such as an electron beam, an ion beam or a neutral corpuscular beam or an electromagnetic wave such as X-rays are applied to the surface of a sample; a pickup step in which a second electromagnetic wave emitted by each of the elements present in the neighborhood of the surface of the sample as a result of excitation in the radiation step is picked up at angles of a range that includes the angle of total reflection of the second electromagnetic wave from the sample surface; a reflection step in which all of the second electromagnetic waves thus picked up are subjected to total reflection; and a detection step in which the totally reflected second electromagnetic waves are subjected to spectroscopy for detection.

According to yet another embodiment of the present invention, there is provided a method of elemental analysis that is similar to the immediately preceding embodiment above except that the incident electromagnetic wave is allowed to fall on the surface of the sample at angles of a range that includes the angle of total reflection of that electromagnetic wave from the sample surface.

According to another embodiment of the present invention, there is provided an elemental analyzer comprising: an excitation source that excites more than one element present in the neighborhood of the surface of a sample to emit the characteristic X-ray of that element; a slit for picking up the emitted characteristic X-ray at angles of a range that includes the angle of total reflection of that characteristic X-ray from the sample surface; a curved mirror or a mirror assembly that consists of the combination of two or more plane mirrors, said mirror or mirror assembly causing total reflection of the characteristic X-rays that have passed through the slit; and an X-ray detector that detects the characteristic X-ray reflected from the mirror or mirror assembly.

According to another embodiment of the present invention, there is provided an elemental analyzer that is similar to the embodiment described immediately above except that the curved mirror has its reflecting surface composed of different materials in different areas or that the mirror assembly consists of the combination of two or more plane mirrors having reflecting surfaces made of different materials.

According to another embodiment of the present invention, there is provided an elemental analyzer that is similar to the embodiment described immediately above same as recited in claim 5 except that the curved mirror or the mirror assembly has a curvature in two axial directions, whereby the X-rays passing through the slit are totally reflected and subsequently focused.

BRIEF DESCRIPTION OF THE DRAWINGS

FIG. 19 is a diagrammatic view showing a prior art elemental analyzer;

DETAILED DESCRIPTION OF THE INVENTION

Figure 1:
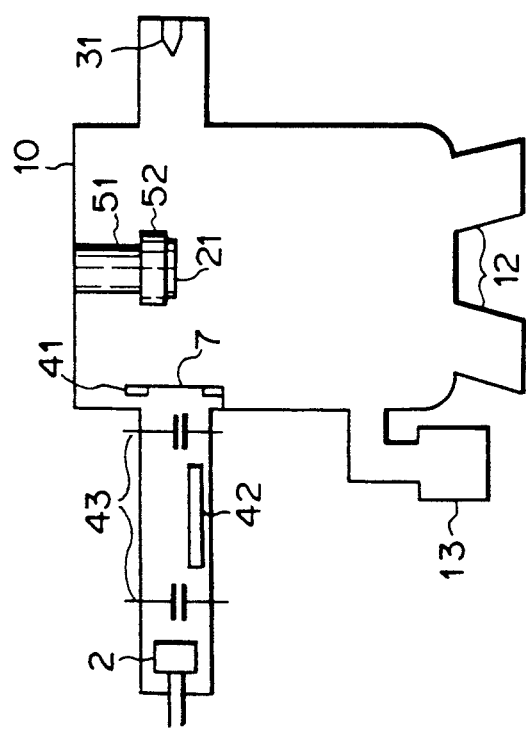
FIG. 1 is a diagrammatic view showing a thin-film forming apparatus according to an embodiment of the first aspect of the present invention.

The mirror for total reflection of X-rays that is used in the thin-film forming apparatus of the present invention is such that the higher the energy of X-rays having a certain glancing angle, the lower the reflectance of the mirror (M. J. Janiak and T. Arai, Abstr. of 1979 Pittsburgh Conf. and Chem. Appl. Spectros., p. 701) and, therefore, by properly setting that mirror and the slits which are capable of adjusting the incident and exit angles of fluorescent X-rays from the sample, as well as the ranges of those angles, two X-rays having different energy levels and, hence, different intensities can be processed to have comparable levels of intensity by means of the combination of the total reflecting mirror and the slits.

Thus, in accordance with one embodiment of the present invention, the constituent elements of the thin film to be formed on the sample are excited with the excitation source to emit fluorescent X-rays and the total reflecting mirror and the slits which are capable of adjusting the incident and exit angles of the emitted fluorescent X-rays, as well as the ranges of those angles are set in such a way that the intensities of those fluorescent X-rays which are emitted from the respective elements become comparable to each other. As a result, when counting the number of pulsed photons in the fluorescent X-rays entering the detector, the counting rate of pulse measurement is in no way limited by the higher of the-two yields of incident fluorescent X-rays and the compositional measurement of the sample can be performed in pace with the rate of thin film formation even if the thin film to be formed contains light elements.

Further, the thin-film forming apparatus of this embodiment of the present invention is equipped with a light and heat shield that is not only heat-resistant but also transmissive of fluorescent X-rays including soft X-rays of 1 keV and less and this is effective in ensuring that the light and heat generated in the process of thin film formation will not cause any adverse effects on the detector, whereby the composition of the sample can be measured consecutively throughout the process of thin film formation.

The total reflecting mirror and the slits in the thin-film forming apparatus of another embodiment of the present invention allow emitted characteristic X-rays to be supplied to the detector in a selective manner so that the characteristic X-rays emitted by a plurality of elements will provide comparable levels of intensity for the detector.

The reflection step of the method for elemental analysis of another embodiment of the present invention is such that the electromagnetic wave picked up in the pickup step is reflected at angles including the angle of total reflection of that electromagnetic wave from the mirror, whereby information from the neighborhood of the surface of the sample is selectively supplied to the detection step.

The radiation step of the method for elemental analysis in one embodiment of the present invention is such that the electromagnetic wave is permitted to fall on the surface of the sample at angles of a range that includes the angle of total reflection of that electromagnetic wave for the sample, whereby only the elements present on the surface of the sample will be excited.

The slits and mirror in the elemental analyzer in another embodiment of the present invention are such that characteristic X-rays are picked up from the sample at angles that include the angle of total reflection while, at the same time, the picked-up characteristic X-rays are allowed to reflect at angles including the angle of total reflection of those characteristic X-rays from the mirror, whereby information from the neighborhood of the surface of the sample is selectively supplied to the X-ray detector.

The mirror in the elemental analyzer of another embodiment of the present invention is such that the angle of reflection varies with the angle at which characteristic X-rays are picked up through the slits, whereby information from the neighborhood of the surface of the sample is selectively supplied to the X-ray detector.

The mirror in the elemental analyzer in another embodiment of the present invention has a curvature in biaxial directions, so that the reflected X-rays are allowed to converge at a point, thereby enabling the detector to detect over a smaller area.

Various embodiments of the present invention are described below with reference to accompanying drawings. FIG. 1 is a diagrammatic view showing the thin-film forming apparatus that enables the composition of a sample to be measured even if a thin film containing light elements is to be formed on the sample. Shown by 42 in FIG. 1 is a mirror, typically made of soda lime glass, for total reflection of X-rays 43 is a slit that is provided at both the entrance and exit of the mirror 42 and that is capable of setting incident and exit angles of fluorescent X-rays that fall upon and emerge from the mirror 42, as well as the ranges of those angles; 41 is a shield of the light and heat generated from a sample making mechanism 12, said shield being not only heat-resistant but also transmissive of fluorescent X-rays including soft X-ray rays of 1 keV and below.

The operation of the thin-film forming apparatus is described below in detail. Fluorescent X-rays entering through the shield 41 can be adjusted by means of slits 43 in such a way that the fluorescent X-rays emitted by the individual elements in the sample 21 will have comparable levels of intensity, which are subsequently detected with a detector 2. The shield 41 effectively isolates detector 2 from any of the light and heat that is generated in the mechanism 12. Further, the shield 41 is so much heat-resistant that it will neither deform nor melt by the heat of radiation from the substrate and other components that are heated during thin film formation and, therefore, the emitted fluorescent X-rays can be measured consecutively throughout the process of thin film formation.

Figure 2:
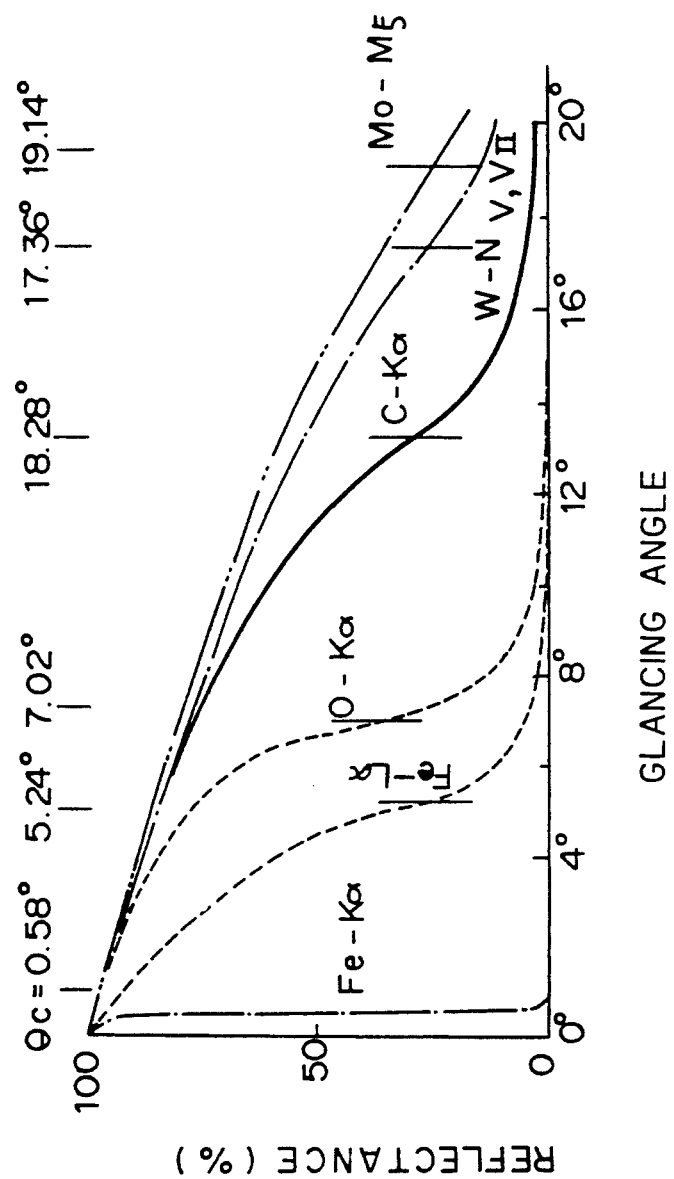
FIG. 2 is a graph showing the relationship between glancing angle and the reflectance of a total reflecting mirror.

FIG. 2 is a graph showing the reflectance of soda lime glass mirror for the incident characteristic X-rays that are emitted by various elements. Obviously, the higher the energy of X-rays, the lower the reflectance of the mirror at a given glancing angle. This feature is utilized in the present invention in such a way that the ranges of incident and exit angles of X-rays onto and from the mirror 42 are properly adjusted by means of the slits 43, whereby the detector 2 can be supplied with two X-rays having comparable levels of intensity even if X-rays having different energy levels are emitted from the sample.

In the thin-film forming apparatus, the excitation source 31 excites the thin film forming on the sample 21 so that the respective elements in the thin film will emit their own characteristic X-rays. The emitted characteristic X-rays pass through the slit 43 at the entrance to fall on the total reflecting mirror 42, from which they are reflected to pass through the slit 43 at the exit to be supplied to the detector 2. As already mentioned, the slits 43 are set in such a way that the characteristic X-rays from the individual elements that have been reflected by the mirror 42 will have comparable levels of intensity before they are supplied into the detector 2. Therefore, the respective characteristic X-rays can be pulse measured with the detector 2 and yet the counting rate will not be limited by the higher of the yields of those characteristic X-rays. In other words, the composition of the sample 21 can be measured at a speed in pace with the rate of thin film formation even if the thin film to be formed on the sample contains light elements.

Figure 3:
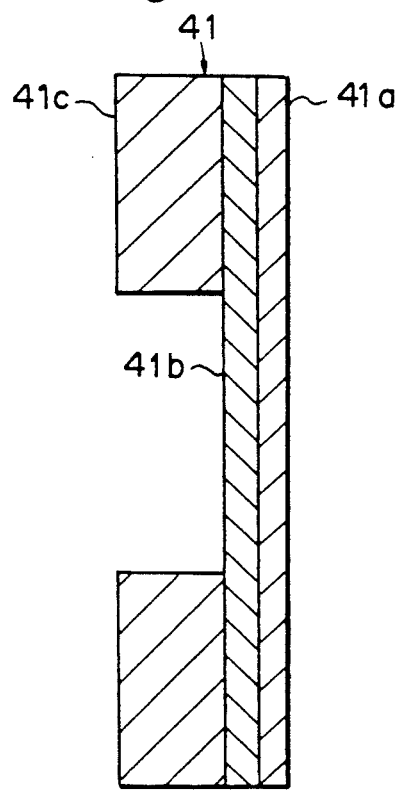
FIG. 3 is a diagrammatic view showing an exemplary shield.

The shield 41 may typically have a structure as shown in FIG. 3. The shield has a thin metal film 41 that is made of a material of small atomic number such as Al or Be, so that it permits the passage of soft X-rays having an energy of 1 keV and less. The metal film 41a is made to be thinner than the conventional X-ray transmitting window 7. Because of its thinness, the metal film 41a is less effective in dissipating the heat of radiation and, to solve this problem, the shield 41 is provided with a support film 41b having good heat conductivity. The support film 41b desirably satisfies the requirements of good transmission of soft X-rays and high physical strength and may typically be formed of polycrystalline or amorphous boron nitride (BN). The shield 41 is also provided with a Si support 41c not only for supporting the thin metal film 41a and the support film 41b but also for facilitating the fabrication of the shield 41.

The shield 41 protects the detector 2 by preventing the entrance of heat and light. Further, the shield 41 which has heat resistance will not be deformed by the heat of radiation from the substrate and other components that are heated during thin film formation. Therefore, the thin-film forming apparatus under consideration is capable of consecutively measuring the characteristic X-rays that are emitted during thin film formation.

Figure 4:
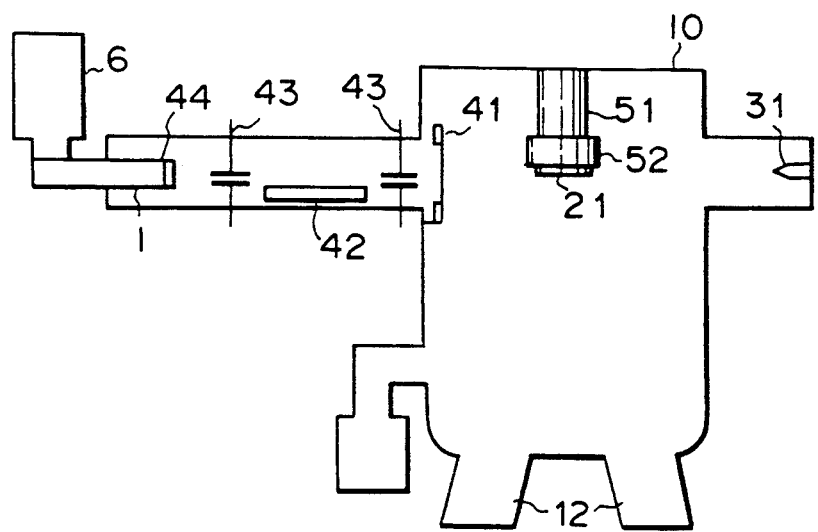
FIG. 4 is a diagrammatic view showing a thin-film forming apparatus according to another embodiment of the first aspect of the present invention.

In the embodiment described above, the detector 2 is adapted to be exposed to air atmosphere but if it is necessary to keep the detector 2 in vacuum at all times, the design shown in FIG. 4 may be adopted. Shown by 44 is a mechanism that partly opens and closes the front of the vessel 1. This construction assures that even if the vacuum in the chamber 10 is broken in certain situations such as servicing of the thin-film forming apparatus, the mechanism 44 needs only to be closed so as to maintain high vacuum around the detector 2.

Figure 5:
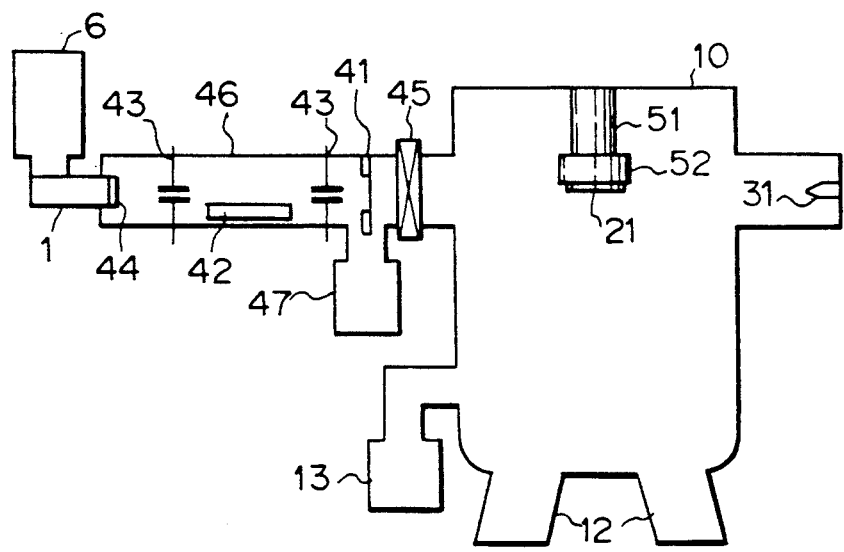
FIG. 5 is a diagrammatic view showing a thin-film forming apparatus according to yet another embodiment of the first aspect of the present invention.

FIG. 5 shows the case where a gate valve 45 is provided to render the unbakable area amenable to desorption when baking the vacuum chamber 10. When installing the system, an exhaust unit 47 provided independent of the exhaust unit 13 on the chamber 10 is activated to draw a vacuum from a vacuum box 46 (the area to be subjected to desorption) and, therefore, the gate valve 45 is opened to achieve the same effect as described in the preceding paragraph.

Figure 6:
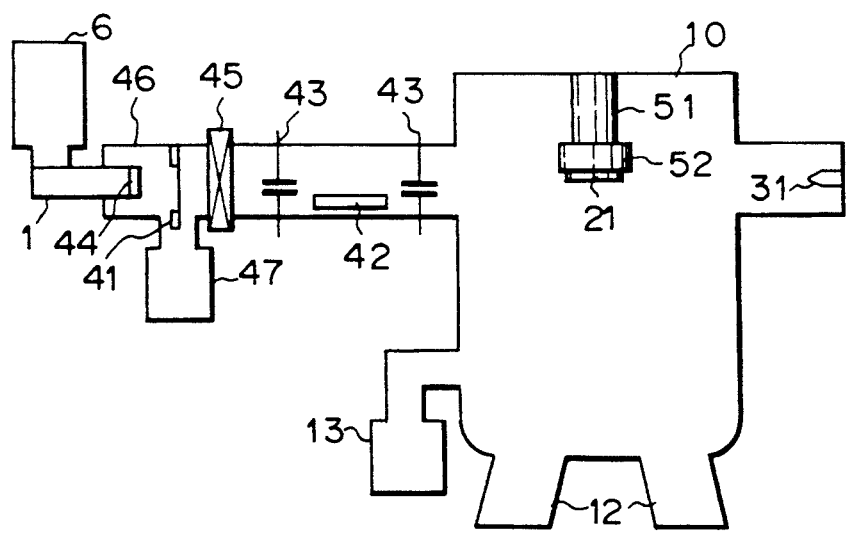
FIG. 6 is a diagrammatic view showing a thin-film forming apparatus according to a further embodiment of the first aspect of the present invention.

When the vacuum chamber 10 in the apparatus shown in FIG. 4 is baked, the detector is also placed in a heated atmosphere. The detector in common use is frequently of such a type that it will break upon heating, so it is desirably dismounted when baking the vacuum chamber 10. FIGS. 5 and 6 show such a desired type of apparatus, in which a vacuum box including the detector is designed to be detachable from the vacuum chamber 10. The apparatus is fitted with a gate valve 45 that is to be opened in order to retain the necessary degree of vacuum in the vacuum chamber 10 after the vacuum box is detached from the chamber. The procedure for operating the apparatus of interest is briefly described below with reference to FIGS. 5 and 6.

First, gate valve 45 is closed and the vacuum box 46 is dismounted, with the vacuum chamber 10 being then baked. After the end of the baking, the vacuum box 46 is replaced and an exhaust unit 47 is activated to draw a vacuum from the vacuum box 46 (if the gate valve 45 is opened with the vacuum box 46 remaining open to air atmosphere, the exhaust unit 13 may break or the degree of vacuum may deteriorate to introduce difficulty in preparing samples. After an adequate degree of vacuum is created in the vacuum box 46, the gate valve 45 is opened, whereupon the system becomes equivalent to the apparatus shown in FIG. 4 and the result is the same as obtained with that apparatus.

The same result can also be attained by providing the shield 41 and gate valve 45 between the vessel 1 and the slit 43 at the exit of the mirror 42.

The foregoing embodiments concern the case of shortening the time to measure the composition of a sample in a thin-film forming apparatus. It should, however, be noted that the basic concept of the present invention is also applicable to the purpose of shortening the time of compositional measurements with a conventional composition analyzer.

Figure 7:
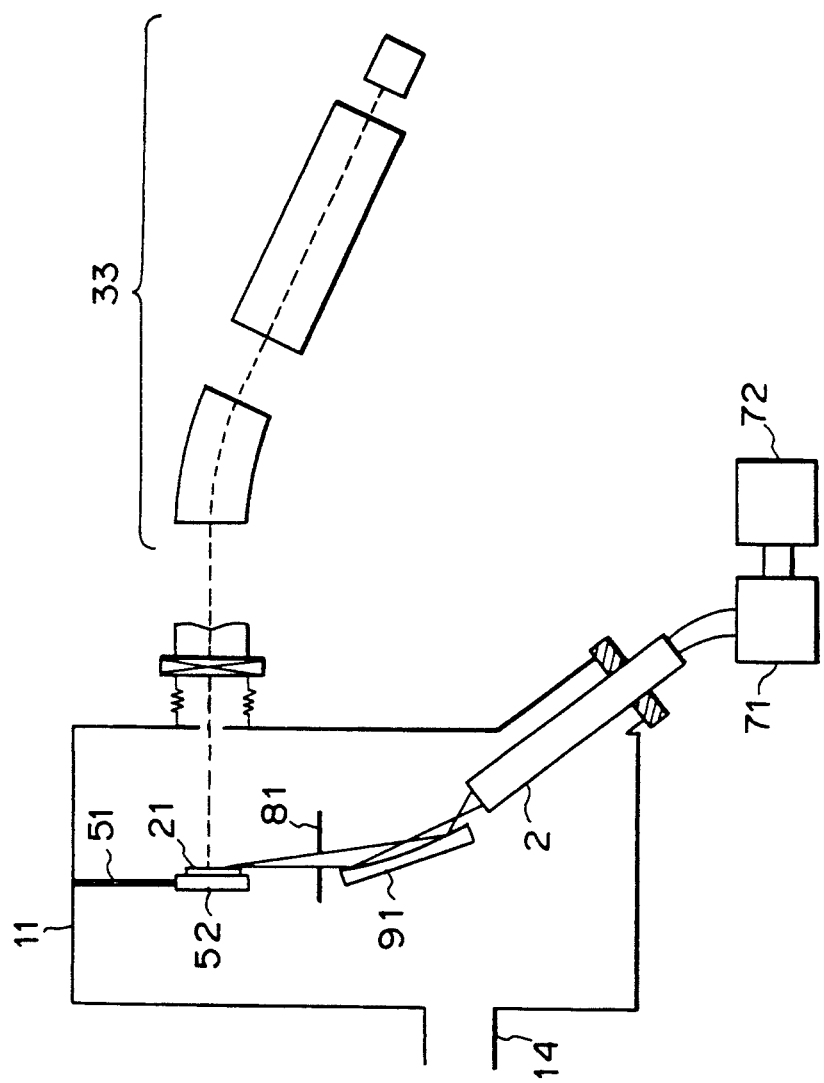
FIG. 7 is a diagrammatic view showing an elemental analyzer according to an embodiment of the second aspect of the present invention.

FIG. 7 is a diagrammatic view of an elemental analyzer that is realized by applying the method of elemental analysis of the present invention to particle induced X-ray emission (PIXE) spectroscopy. Shown by 33 in FIG. 7 is an ion-beam accelerator; 81 is a slit for picking up X-rays; and 91 is a mirror for reflecting X-rays. The other components of the system shown in FIG. 7 are the same as those shown in FIG. 19 and are identified by like numerals.

The operation of the system shown in FIG. 7 is described below. The ion beam accelerator 33 applies an accelerated ion beam onto the sample 21, whereupon the element as excited by the ion beam emits its own characteristic X-ray. The opening of the slit 81 is so set that the emitted characteristic X-ray can be picked up at angles including the angle of total reflection. Hence, all characteristic X-rays that are picked up at the angle of total reflection will be permitted to fall on the mirror 91, which reflect those X-rays. The reflected X-rays are detected with the detector 2 and fed through the spectrum analyzer 71, with the resulting X-ray spectra being stored in the memory unit 72. As in the conventional case, the memory unit 72 may be replaced by a display unit.

Figure 23:
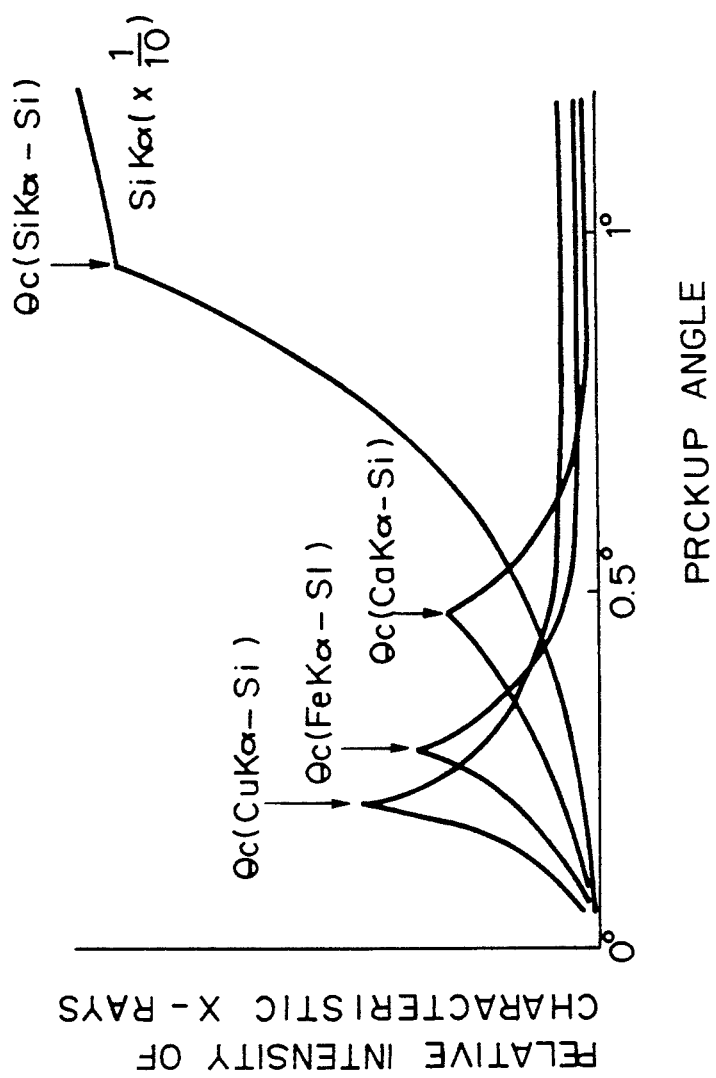
FIG. 23 is a graph showing the pickup angle dependency of the characteristic X-rays emitted by various elements, Ca, Fe and Cu that are deposited in very small amounts on the Si surface.
Figure 24:
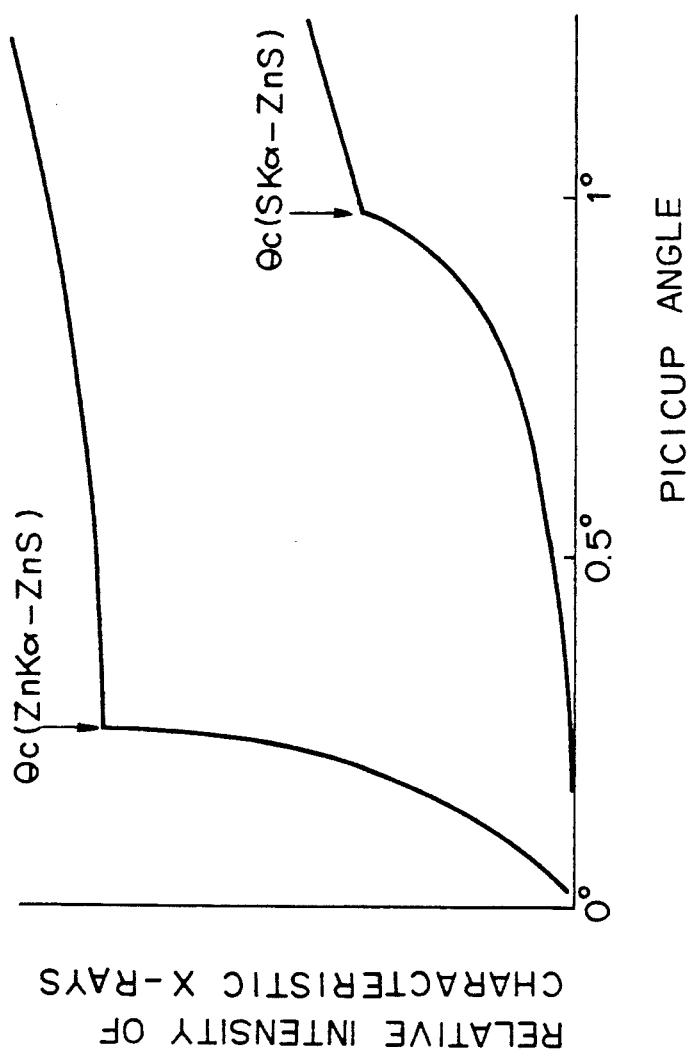
FIG. 24 is a graph showing the pickup angle dependency of the characteristic X-rays emitted from a ZnS sample.

Let us describe here the case where Ca, Fe and Cu are deposited as trace impurities on the surface of the Si sample 21. The intensity of characteristic X-ray vs the angle at which it is picked up from the associated element is as plotted in FIG. 23. In view of FIG. 23 (or eq. 1), the angles of total reflection of Ca, Fe and Cu characteristic X-rays with respect to Si are 0.48°, 0.27° and 0.21°, respectively. Hence, the opening of the slit 81 is set in such a way that it will permit the passage of X-rays that issue from the surface of the sample 21 at angles including 0.48°–0.21°.

The X-rays passing through the slit 81 are reflected by the mirror 81 at certain angles. In this case, characteristic X-rays having the lower energy are totally reflected at larger angles and those characteristic X-rays which are picked up at the angles of total reflection for the lower energy also contain characteristic X-rays of the higher energy. Since the angle of total reflection of those characteristic X-rays having the higher energy is smaller than that for the lower energy, information from deep areas is also contained in the X-rays picked up at the angle of total reflection for the lower energy. By insuring that the characteristic X-rays picked up at that angle of total reflection are reflected by the mirror 91 at a certain angle, the characteristic X-rays of the higher energy can be attenuated because of the relationship shown in FIG. 8. By repeating this procedure at the angles of total reflection for the respective elements of interest, information about more than one element in the neighborhood of the sample's surface can be selectively obtained for elemental analysis.

Figure 8:
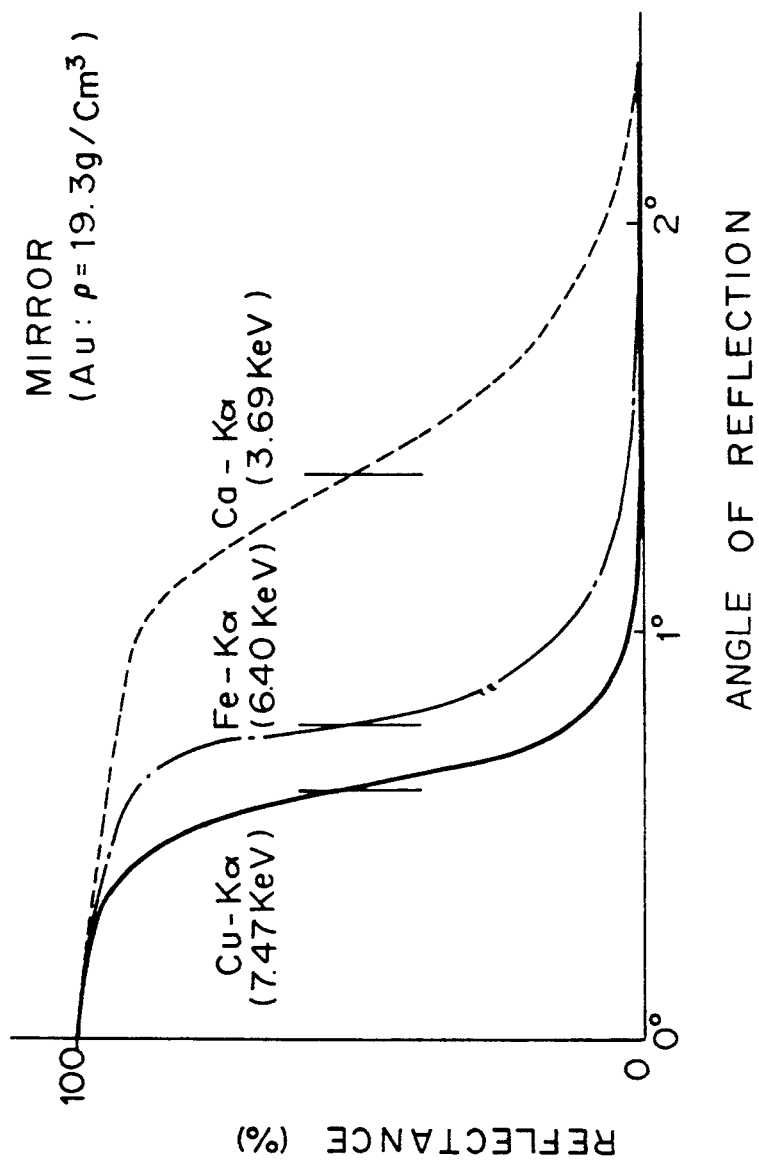
FIG. 8 is a graph showing the relationship between the angle of reflection by a gold (Au) mirror and its reflectance.

Take, for example, the case where the mirror 91 is made of gold (Au). The reflectance of the characteristic X-ray for each element vs the angle of reflection is as shown in FIG. 8. Hence, if the system is set in such a way that the X-ray picked up at the angle 0.48° (which is the angle of total reflection of the Ca characteristic X-ray with respect to Si and that is greater than the angles of total reflection for Fe and Cu) is incident on the surface of mirror 91 at 1.39°, those X-rays which are reflected at that angle of reflection and that are characteristic of Fe and Cu are attenuated. In other words, the Fe and Cu characteristic X-rays containing information from the deeper area of sample 21 are attenuated.

If the system is set in such a way that the X-ray picked up at the angle 0.27° (which is the angle of total reflection of the Fe characteristic X-ray with respect to Si and that is greater than the angle of total reflection for Cu) is incident on the surface of mirror 91 at 0.77°, those X-rays which are reflected at that angle of reflection and that are characteristic of Cu are attenuated. In other words, the Cu characteristic X-ray containing information from the deeper area of sample 21 is attenuated. Further, the system is set in such a way that the X-ray picked up at the angle 0.21° (which is the angle of total reflection of the Cu characteristic X-ray for Cu) is incident on the surface of the mirror at an angle smaller than 0.61°, to thereby insure that said incident X-ray will not be attenuated. In this way, the characteristic X-ray for each of the elements of interest can be picked up with the effect of the X-rays for other elements being adequately reduced. In addition, an ion beam is used as an excitation source, so the dose of X-rays due to Bremsstrahlung (deceleration radiation) can be reduced, to thereby reduce the background of detected X-rays.

Figure 9:
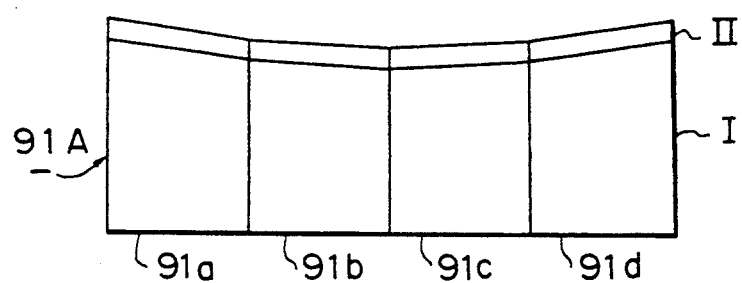
FIG. 9 is a diagrammatic view showing an exemplary mirror structure.

Since the energy levels of the characteristic X-rays for respective elements take on discrete values, several plane mirrors may be combined together (in the case shown in FIG. 9, four plane mirrors 91a–91d are combined) in the manner described below to construct a mirror assembly 91A that is capable of attaining the result already described above. An X-ray picked up by the slit 81 at any one of the designated angles (0.48°, 0.27° and 0.21° in the case discussed above) is allowed to be incident on a certain of the associated plane mirrors 91a–91d while, at the same time, those plane mirrors 91a–91d are set in such a way that they will reflect the incident X-rays at appropriate angles (at 1.39°, 0.77° and at less than 0.61° in the case discussed above). If desired, the base of the mirror assembly 91A (as indicated by I in FIG. 9) may be made of quartz ($SiO_2$), silicon carbide (SiC) or some other material whereas an Au film about 1000 Å thick is evaporated on the surface of the assembly (as indicated by II), and this type of mirror assembly will work in the same manner as if it were totally made of Au.

Figure 10:
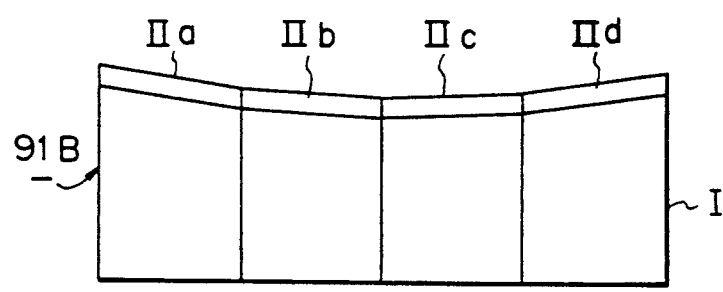
FIG. 10 is a diagrammatic view showing another exemplary mirror structure.

In the foregoing embodiment, the energy level of the characteristic X-ray selected by the mirror 91 and, hence, the characteristic X-ray selected, is varied by changing the angle of incidence on the surface of the mirror 91. However, according to eq. 1, the angle of total reflection varies with the density of mirror 91, so the energy level selected can be varied by changing the material of which the mirror is made. Thus, the energy level to be filtered can be varied. FIG. 10 shows an example of the mirror assembly that is constructed on the basis of this principle. The mirror assembly generally indicated by 91B is composed of various mirror materials IIa–IId that are selected in such a way that materials of the lower density are used in association with X-rays that are picked up at larger angles of total reflection whereas those of the higher density are used in association with X-rays that are picked up at smaller angles of total reflection. The mirror assembly 91B constructed in the manner described above also achieves the same results as in the previous embodiments.

Figure 11:
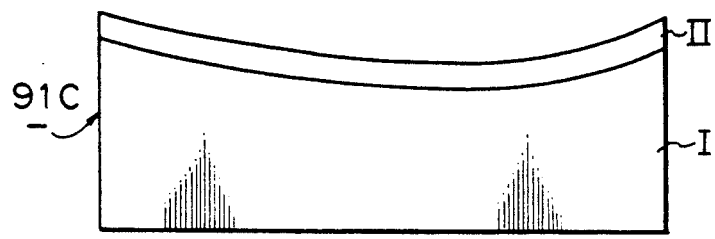
FIG. 11 is a diagrammatic view showing still another exemplary mirror structure.

Another example of the mirror 91 is a curved mirror as indicated by 91C in FIG. 11. This curved mirror 91C has the advantage of dealing with a greater variety of elements. To this end, the curvature of the mirror 91C is set in such a way that when X-rays are incident at angles at which they were picked up by the slit 81, they are reflected by the mirror 91C at respective appropriate angles. If desired, the surface of the curved mirror 91C may be formed of different materials depending on position.

Figure 12:
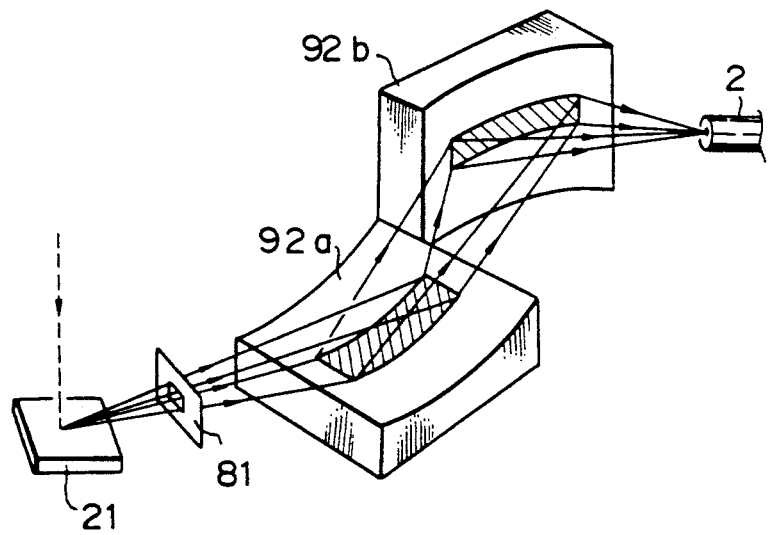
FIG. 12 is a perspective view showing the principal part of an elemental analyzer according to another embodiment of the second aspect of the present invention.

If the angle of incidence on the mirror 91 and the material of which the mirror surface is made are properly selected, it is possible for the mirror 91 to work as an optical filter while focusing the reflected X-rays at a point. To this end, two cylindrical mirrors 92a and 92b having an elliptical cross section are provided as shown in FIG. 12. With this arrangement, the point at which elemental excitation occurs to emit characteristic X-rays is brought into registry with one of the two foci of the ellipsis and the surface of one mirror 92a is made of an appropriately selected material to provide a filtering action whereas the other mirror 92b positioned perpendicular to the mirror 92a focuses the incident X-rays to converge at a point. The advantage of this arrangement is that the area of the detector 2 necessary for detection is sufficiently reduced to improve the resolution and, hence, the precision of analysis. X-rays can also be focused at a point by means of a single mirror having a curvature in the direction of z-axis.

With the above-described arrangement in which the elemental analyzer is composed of a curved mirror, a multiple of trace metal elements in a biosample can be analyzed with high sensitivity. To this end, a biosample is placed on the surface of a C substrate and the opening of the slit 81 is set in such a way that X-rays can be picked up at angles less than the angle of total reflection for C, whereby the X-rays picked up at the angles of total reflection for the respective elements to be analyzed are reflected by the appropriate mirror as described above to enable the various elements to be measured with high sensitivity. In this case, by picking up the X-rays at angles less than the angle of total reflection for C, the intensity of the X-rays that are characteristic of C and that are launched into the detector 2 can be sufficiently reduced to enhance the sensitivity for the sample on the surface of the C substrate.

Figure 13:
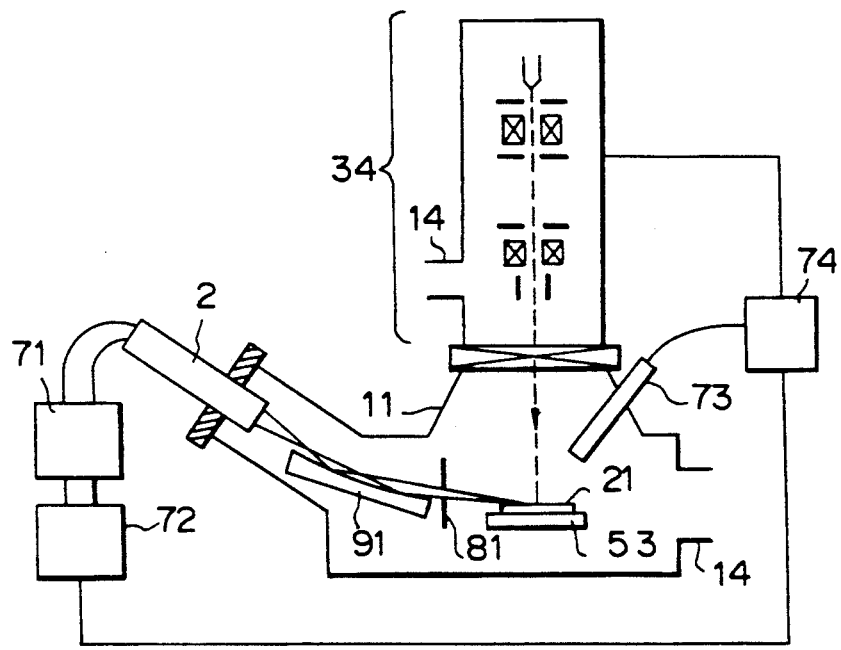
FIG. 13 is a diagrammatic view showing an elemental analyzer according to still another embodiment of the second aspect of the present invention.

FIG. 13 is a diagrammatic view of an elemental analyzer that is realized by applying the method of elemental analysis of the present invention to electron probe microanalysis (EPMA). Shown by 34 in FIG. 13 is an electron beam accelerator; 53 is an X-Y stage; 73 is a secondary electron detector; and 74 is an electron beam controller for scanning electron beams. The other components of the system shown in FIG. 13 are the same as those shown in FIG. 7 and are identified by like numerals.

In the elemental analyzer having the construction outlined above, an electron beam as accelerated by the accelerator 34 in response to the scanning with the controller 74 is applied to the sample 21, whereupon the elements as excited by the incident electron beam will emit their own characteristic X-rays. As in the case of the preceding embodiments, the emitted characteristic X-rays are filtered by passage through the slit 81 and reflection by mirror 91 before they are launched into the detector 2. The output from the detector 2 is passed through the spectrum analyzer 71 and the resulting X-ray spectra are stored in the memory unit 72. Alternatively, the X-ray spectra are displayed on the screen of a display unit.

Hence, as in the case of the preceding embodiments, the elements present in the neighborhood of the surface of the sample 21 can be measured with high sensitivity. What is unique about this embodiment is that the controller 74 is adapted to scan the exciting electron beam whereas the secondary electron detector 73 detects the secondary electrons emitted from the sample 21, thereby making it possible to obtain a secondary electron image of each element simultaneously with its analysis. As a result, imaging of the surface of the sample 21 and elemental analysis of the neighborhood of that surface can be accomplished simultaneously in the memory unit 72 or display unit.

Figure 14:
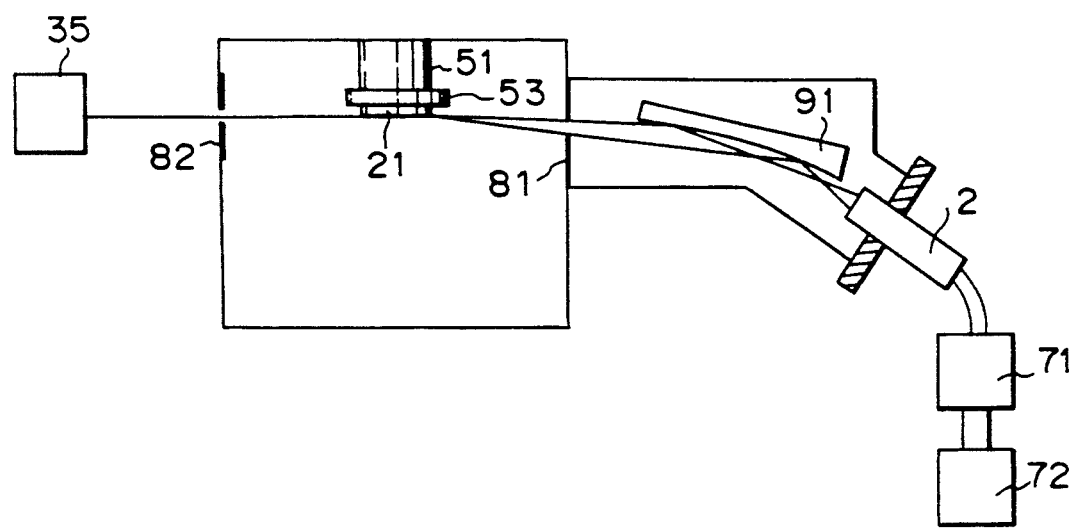
FIG. 14 is a diagrammatic view showing an elemental analyzer according to yet another embodiment of the second aspect of the present invention.

FIG. 14 is a diagrammatic view of an elemental analyzer that is realized by applying the method of elemental analysis of the present invention to total reflection X-ray fluorescence (TRXRF) spectroscopy. Shown by 35 in FIG. 14 is an X-ray source; 53 is an X-Y stage; 82 is a slit through which the X-rays from the source 35 are applied to the sample 21 at the angle of total reflection or at nearby angles. The other components of the system shown in FIG. 14 are the same as those shown in FIG. 7 and hence are identified by like numerals.

In the system shown in FIG. 14, X-rays generated by the X-ray source 35 are adjusted by the slit 82 in such a way that they are applied to the sample 21 at the angle of total reflection or at nearby angles. The elements in the surface of the sample 21 are excited by the incident X-rays to emit their own characteristic fluorescent X-rays, which are then picked up by the slit 81 at angles including the angle of total reflection. As in the case of the previous embodiments, the X-rays thus picked up are reflected by the mirror 91, then detected with the detector 2 and passed through the spectrum analyzer 71, with the resulting X-ray spectra being stored in the memory unit 72. Alternatively, the X-ray spectra may be displayed on the screen of a display unit.

Hence, as in the case of the preceding embodiments, the elements present in the neighborhood of the surface of the sample 21 can be measured with high sensitivity. What is unique about this embodiment is that since the X-rays from the X-ray source 35 are adjusted by the slit 82 to be incident on the sample 21 at the angle of total reflection or at nearby angles, only the elements in the surface of the sample 21 will be excited by the applied X-rays and no fluorescent X-rays will be emitted from the deeper area of the sample. This contributes to a further improvement in the sensitivity of surface measurement. If desired, the X-rays from the X-ray source 35 that have been reflected by the sample 21 may be blocked by the slit 81 of the direction of their detection may be offset from the direction of X-ray radiation so that they will not interfere with the intended measurement. In another embodiment, a synchrotron radiation may be used as the X-ray source 35.

It is also possible to use the elemental analyzer under discussion as an apparatus for inspecting the surface of Si wafers to check for the presence of impurities. In this case, more than one unit of slit 81, X-ray reflecting mirror 91 and detector 2 may be provided to enhance the sensitivity for detection.

The description of the foregoing embodiments centers on the case of using an electron beam or an ion beam. It should, however, be noted that a neutral corpuscular beam can also be used as the excitation beam and this has the advantage of avoiding the problem of charge-up which would otherwise be caused by charged corpuscular beams if the sample 21 is an insulator.

Figure 15:
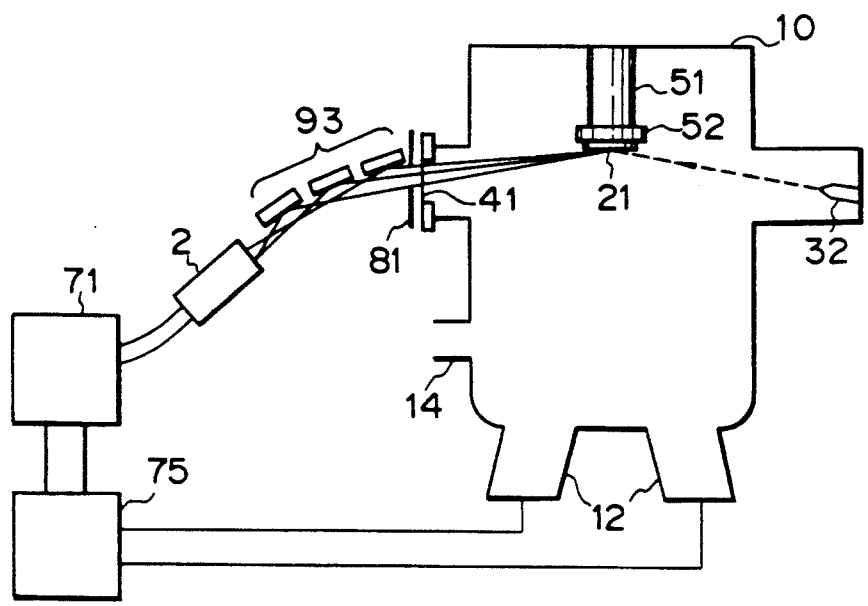
FIG. 15 is a diagrammatic view showing a thin-film forming apparatus to which is applied a method of elemental analysis according to an embodiment of the third aspect of the present invention.

FIG. 15 is a diagrammatic view of a thin-film forming apparatus that incorporates the method of elemental analysis of the present invention. Shown by 32 in FIG. 15 is an electron gun; 81 is a slit for picking up X-rays; 93 is a mirror assembly; and 75 is a controller that includes a memory unit or a display unit and that controls a sample making mechanism 12. The other components of the system shown in FIG. 15 are the same as those shown in FIG. 1 and hence are identified by like numerals.

The operation of the system shown in FIG. 15 is described below. The electron beam issuing from the electron gun 32 is applied onto the surface of the sample 21, whereupon the elements present in the surface of the sample 21 or in its neighborhood are excited by the incident electron beam to emit their own characteristic X-rays. The emitted characteristic X-rays are picked up by the slit 81 at angles including the angle of total reflection. The X-rays passing through the slit 81 are reflected by the mirror assembly 93 and subsequently detected by the detector 2. The output of the detector 2 is spectrum separated by the spectrum analyzer 71 and the resulting X-ray spectra are stored or displayed in the controller 75. The mirror assembly 93 is composed of a plurality of plane mirrors (three mirrors are shown in FIG. 15) that are capable of tilting independently of one another to achieve the same effect as the mirror 91 shown in FIG. 7.

As described above, the method of elemental analysis according to the present invention is applied to a thin-film forming apparatus and this enables information on the composition of the sample in the neighborhood of the surface to be obtained with high sensitivity. A homogeneous thin film (having the same composition irrespective of depth) can be formed by controlling the sample making mechanism 12 on the basis of the thus obtained information.

The applicability of this technique for elemental analysis is not limited to the thin-film forming apparatus and it may be applied to an etching or other apparatus so as to check for the degree of contamination of the sample's surface with impurities that can take place in the interior of those apparatus.

Figure 16:
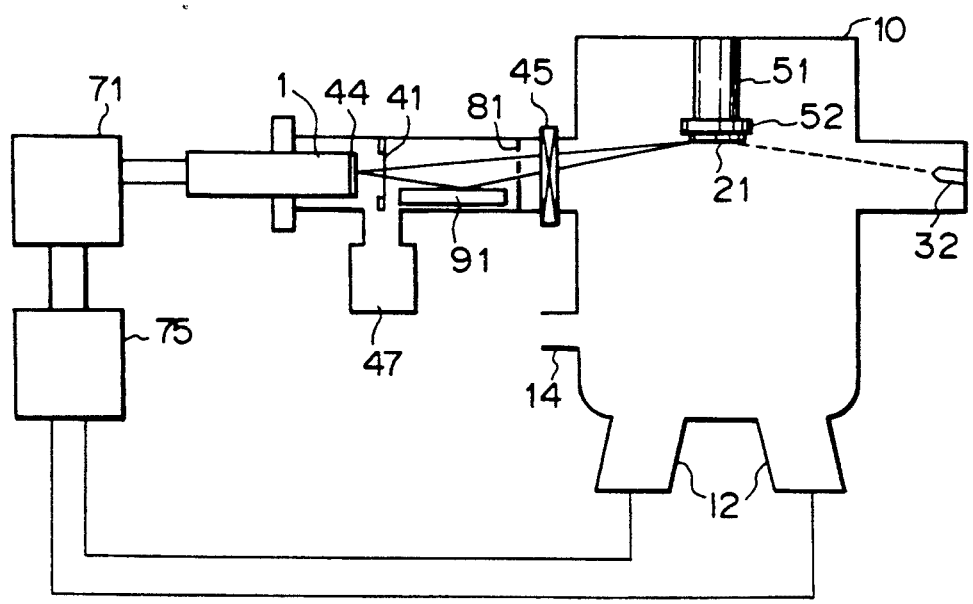
FIG. 16 is a diagrammatic view showing a thin-film forming apparatus to which is applied a method of elemental analysis according to another embodiment of the third aspect of the present invention.
Figure 17:
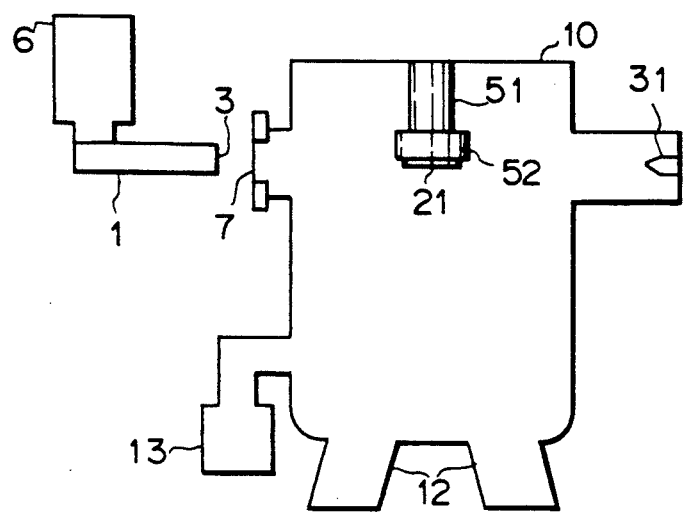
FIG. 17 is a diagrammatic view showing a prior art thin-film forming apparatus.
Figure 18:
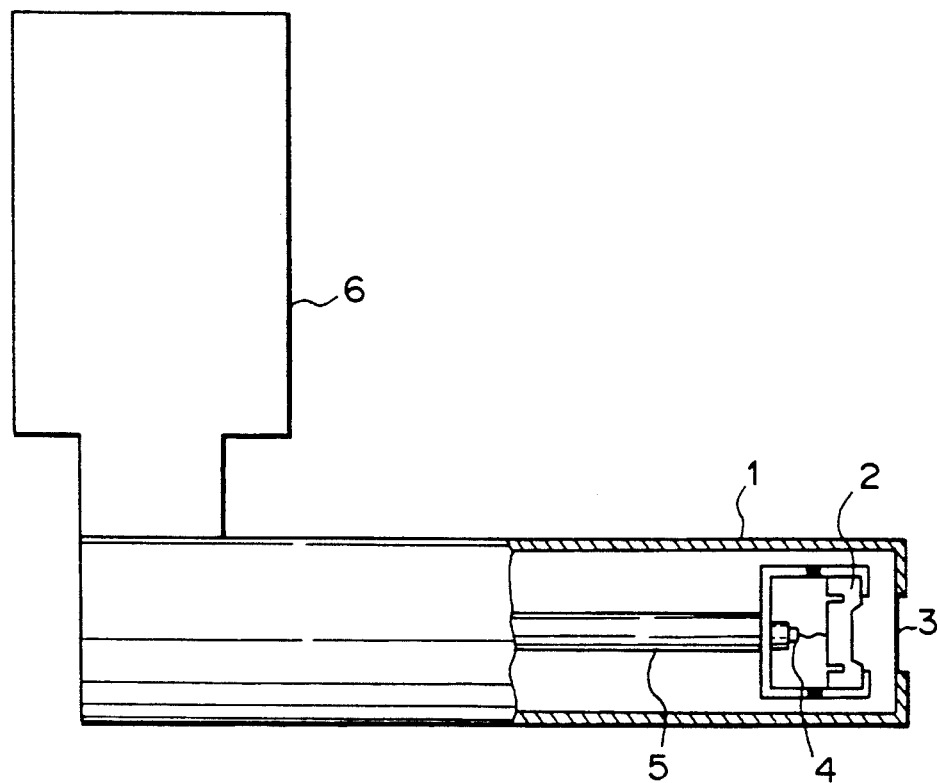
FIG. 18 is a diagrammatic view showing the structure of a vessel accommodating an X-ray detector.
Figure 20A:
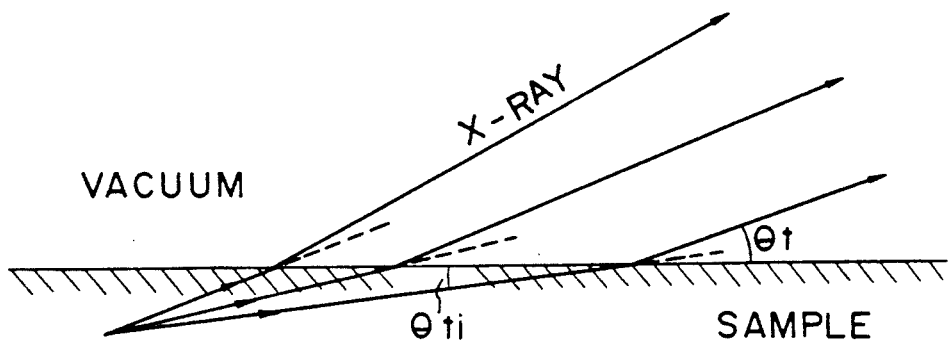
FIG. 20 is a set of diagrams showing how X-rays are refracted.
Figure 20B:
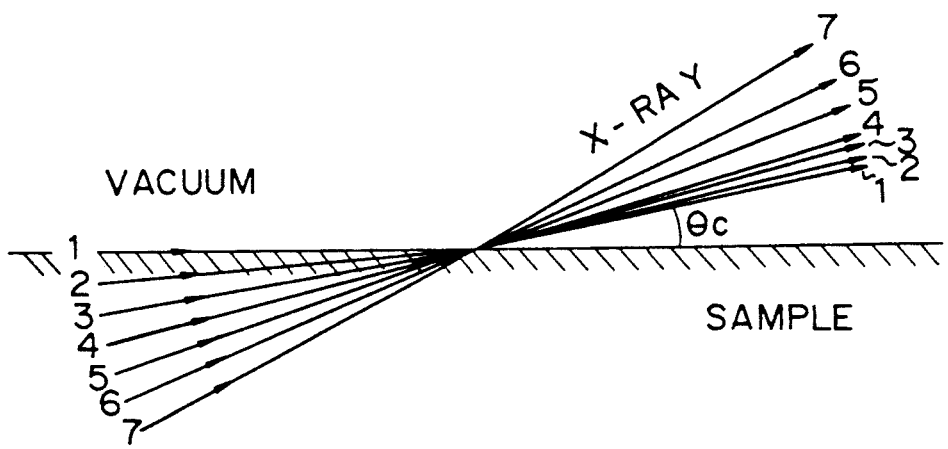
Figure 21:
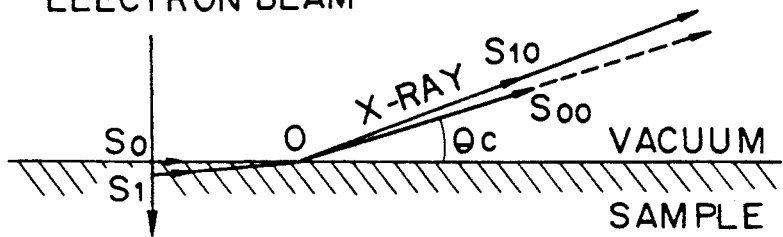
FIG. 21 is a diagram showing how the characteristic X-rays emitted by excitation with an electron beam are refracted.
Figure 22:
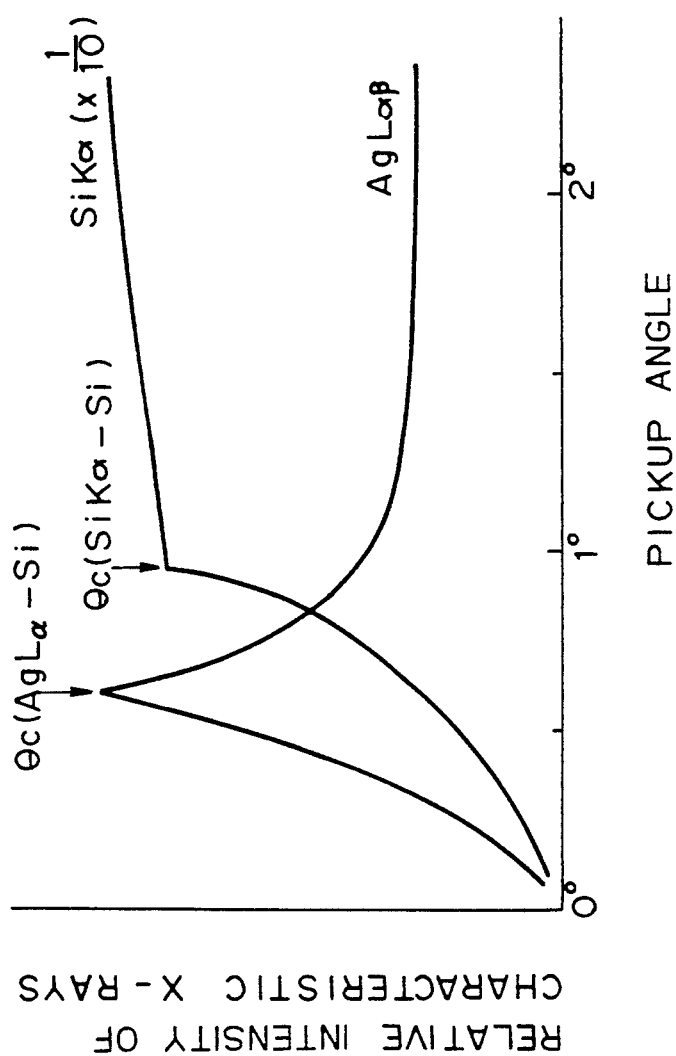
FIG. 22 is a graph showing the pickup angle dependency of the characteristic X-rays emitted from a sample having approximately one atomic layer of Ag evaporated on the Si surface.

FIG. 16 is a diagrammatic view of another thin-film forming apparatus that incorporates the method of elemental analysis of the present invention. Shown by 41 in FIG. 16 is a shield that isolates the detector 2 from heat and light and that is transmissive of X-rays including soft X-rays of 1 keV and less; 44 is an opening/closing mechanism fitted at the front face of the vessel 1 accommodating the detector 2; and 45 is a gate valve. The other components of the system shown in FIG. 16 are the same as those shown in FIG. 15 and hence are identified by like numerals.

The operation of the system shown in FIG. 16 is described below. The electron beam emitted from the electron gun 32 is applied onto the surface of the sample 21. The elements present in the surface of the sample 21 and in its neighborhood are excited by the incident electron beam to emit their own characteristic X-rays, which are picked up by the slit 81 at angles including the angle of total reflection. The X-rays passing through the slit 81 are reflected by the mirror 91 and then detected by the detector 2. The output of the detector 2 is spectrum separated by the spectrum analyzer 71 and the resulting X-ray spectra are either stored or displayed in the controller 75. In the case of forming a thin film of a binary compound, the slit 81 allows the characteristic X-rays from the two elements of interest to be picked up at angles close to the associated angles of total reflection. Since the X-rays picked up at the greater angle of total reflection contain those characteristic X-rays of the higher energy which contain information from the deeper area, such high-energy characteristic X-rays are attenuated by means of the mirror. The reflected X-rays from the mirror 91 which are picked up at the smaller angle of total reflection are detected with the detector 2.

Thus, information on the composition of the sample 21 in the neighborhood of its surface can be obtained with high sensitivity. What is unique about the embodiment shown in FIG. 16 is that the vessel 1 of the detector 2 is equipped with the opening/closing mechanism 44 and that after a vacuum is drawn by degassing with the exhaust unit 47, the mechanism 44 is opened to start measurement. As a further advantage, the provision of the shield 41 that isolates the detector 2 from incoming light and heat and which is transmissive of X-rays including soft X-rays of 1 keV and less insures that even characteristic X-rays from light elements can be measured without any adverse effects of light and heat that are generated from the sample making mechanism 12 or by the heating of the sample 21 itself.

As described on the foregoing pages, the thin-film forming apparatus of one embodiment is such that the light and heat generated from the sample making mechanism is isolated from the detector by means of the shield that is not only heat-resistant but also transmissive of fluorescent X-rays including soft X-rays of 1 keV and less while, at the same time, a mirror for total reflection of X-rays that is equipped with slits capable of adjusting the incident and exit angles of fluorescent X-rays from the sample excited with an excitation source, as well as the ranges of those angles is provided either at the entrance or exit of said shield or at both. Hence, when counting the number of pulsed photons in the fluorescent X-rays entering the detector, the counting rate of pulse measurement is in no way limited by the higher of the two yields of incident fluorescent X-rays and the compositional measurement of the sample can be performed in pace with the rate of thin film formation even if the thin film to be formed contains light elements. Further, it is insured that the light and heat generated in the process of thin film formation will not cause any adverse effects on the detector, whereby the composition of the sample can be measured consecutively throughout the process of thin film formation.

The thin-film forming apparatus of another embodiment is such that the intensity levels of characteristic X-rays for various elements can be adjusted by means of a total reflecting mirror and slits while, at the same time, a shield is provided that is not only heat-resistant but also capable of isolating the X-ray detector from heat and light. Hence, when counting the number of pulsed photons in the fluorescent X-rays entering the detector, the counting rate of pulse measurement is in no way limited by the higher of the two yields of incident fluorescent X-rays and the compositional measurement of the sample can be performed in pace with the rate of thin film formation even if the thin film to be formed contains light elements. Furthermore, the composition of the sample can be measured consecutively throughout the process of thin film formation.

In the method of elemental analysis in another embodiment of the invention, electromagnetic waves are picked up from the surface of a sample at angles including the angle of total reflection of those waves so that the picked-up electromagnetic waves will undergo total reflection. Hence, information on various elements of interest that are present in the surface of the sample and in its neighborhood can be detected with high sensitivity.

In the method of elemental analysis in still another embodiment of the invention, an exciting electromagnetic wave is allowed to be incident on the surface of a sample at angles of a range that includes the angle of total reflection from the sample's surface. Hence, only the elements that are present in the surface of the sample and in its neighborhood are excited but no characteristic X-rays will be emitted from the deeper area of the sample, whereby the sensitivity of surface measurement in elemental analysis can be further enhanced.

The elemental analyzer of another embodiment of the invention is such that the characteristic X-rays for respective elements of interest are picked up at angles of a range that includes the angle of total reflection from the sample's surface and that the picked-up X-rays are reflected at angles that are associated with the respective elements. Because of this feature, information on the respective elements can be obtained without lowering the sensitivity for surface measurement.

The elemental analyzer of another embodiment of the invention is such that the characteristic X-rays for respective elements of interest are picked up at angles of a range that includes the angle of total reflection from the sample's surface and that the picked-up X-rays are reflected by a mirror that is made of different materials depending on the area where the X-rays are incident. Because of this feature, the characteristic X-rays for the desired elements can be reflected while attenuating the X-rays having higher energy levels, whereby information on the elements of interest that are present in the surface of the sample and in its neighborhood can be selectively obtained.

The elemental analyzer in yet another embodiment of the invention is such that the characteristic X-rays for respective elements of interest are picked up at angles of a range that includes the angle of total reflection from the sample's surface and that the picked-up X-rays are reflected at angles that are associated with the respective elements, with the added result that the reflected X-rays are focused at a single point. Because of this feature, the detection area of the X-ray detector can be sufficiently reduced to insure that the resolution of the X-ray detector and, hence, the precision of analysis are improved.

What is claimed is:

1. A thin-film forming apparatus in which the elements in a sample produced in a mechanism by a thin-film forming process in a vacuum chamber are excited by an excitation source to emit associated fluorescent X-rays, comprising:
   a detector for detecting the associated fluorescent X-rays to insure that the composition of said sample is consecutively measured in the process of thin-film formation,
   a shield for isolating the detector from light and heat generated in the mechanism, said shield being heat-resistant and transmissive of at least fluorescent X-rays containing soft X-rays of 1 keV and below,
   a mirror for reflecting the associated flourescent X-rays toward the detector [is provided either at the entrance or exit of said shield or at both,
   and means defining slits capable of adjusting the incident and exit angles of said fluorescent X-rays with respect to the mirror, and the ranges of said angles.

2. The thin-film forming apparatus of claim 1, wherein the mirror is provided at the entrance of said shield.

3. The thin-film forming apparatus of claim 1, wherein the mirror is provided at the exit of said shield.

4. The apparatus of claim 8, further comprising a second mirror for reflecting the associated flourescent X-rays provided at the entrance of said shield.

5. The thin film forming apparatus of claim 1 wherein the shield comprises a thin metal film permitting passage of at least soft X rays having an energy of 1 keV and below;
   a support film attached to said thin metal film and having good heat conductivity;
   and a support for supporting the thin metal film and the support film.

6. The thin film apparatus of claim 5 wherein the thin metal film is made of material of a small atomic number;
   wherein the support film is formed of boron nitride;
   wherein the support is formed of silicon.

7. The thin film forming apparatus of claim 1 further comprising a vacuum box for supporting at least the detector;
   a gate valve disposed between the vacuum box and the vacuum chamber; and
   an exhaust unit for removing air from the vacuum box.

8. The thin film forming apparatus of claim 7 wherein the detector is disposed in a vessel and further comprising a mechanism attached to the vessel for opening and closing the vessel 1.

9. The thin film forming apparatus of claim 1 further comprising a vacuum box for supporting at least the detector;
   a gate valve disposed between the vacuum box and the vacuum chamber; and
   an exhaust unit for removing air from the vacuum box.

10. The thin film forming apparatus of claim 9 wherein the detector is disposed in a vessel and further comprising a mechanism attached to the vessel for opening and closing the vessel.

11. An elemental analyzer comprising:
    an excitation source for exciting more than one element present in the neighborhood of the surface of a sample to emit the characteristic X-ray of that each element;
    means defining a slit for picking up the emitted characteristic X-ray of each element at angles of a range that includes the angle of total reflection of each of said characteristic X-rays from the surface of said sample;
    means for ensuring that said characteristic X-rays passing through said slit are totally reflected at angles corresponding to said individual elements such that the intensities of X-rays emitted by the elements are at a similar level; and
    an X-ray detector for detecting the characteristic X-rays reflected from said means for ensuring.

12. The elemental analyzer of claim 11 wherein the means for ensuring that said characteristic X-rays passing through said slit are totally reflected at angles corresponding to said individual elements comprises a curved mirror.

13. The elemental analyzer of claim 11 wherein the means for ensuring that said characteristic X-rays passing through said slit are totally reflected at angles corresponding to said individual elements comprises a mirror assembly comprising a plurality of plane mirrors.

14. The elemental analyzer of claim 11, wherein the electromagnetic wave is an ion beam generated an ion beam accelerator.

15. The elemental analyzer of claim 11, further comprising a spectrum analyzer for performing spectrum analysis on the detected X-rays wherein results of spectrum analysis are stored in a memory.

16. The elemental analyzer of claim 11, further comprising a spectrum analyzer for performing spectrum analysis on the detected X-rays wherein results of spectrum analysis are displayed on a display unit.

17. The elemental analyzer of claim 11, wherein the means for ensuring that each characteristic X-ray picked up at the respective angle of total reflection is reflected by a mirror at a predetermined angle such that characteristic X-rays of other energies are attenuated.

18. The elemental analyzer of claim 11, further comprising means for ensuring that when X-rays are incident at angles at which they are picked up by the slit, they are reflected by the mirror at respective appropriate angles.

19. The elemental analyzer of claim 11, wherein the electromagnetic waves are fluorescent X-rays, wherein the elemental analyzer further comprises means defining a slit through which X-rays from the X-ray source are applied to the sample at the angle of total reflection or at nearby angles, whereby only the elements in the surface of the sample are excited by the applied X-rays and no fluorescent X-rays are emitted from the deeper area of the sample.

20. A thin-film forming apparatus comprising:
a mechanism in a vacuum chamber for producing a sample by a thin-film forming process; and
an elemental analyzer for measuring the composition of said sample as it is produced, said elemental analyzer comprising:
an excitation source that excites the elements in said sample to emit characteristic X-rays;
a total reflecting mirror for reflecting said characteristic X-rays;
an X-ray detector for detecting the characteristic X-rays as reflected from said total reflecting mirror;
means for defining slits that determine the range of incident angles for the characteristic X-rays that are to be incident on said total reflecting mirror, as well as the range of exit angles for those characteristic X-rays which have been reflected from said total reflecting mirror and which reach said detector; and
a shield for isolating said X-ray detector from light and heat and that is heat-resistant and transmissive of at least fluorescent X-rays containing soft X-rays of 1 keV and below.

21. The thin film forming apparatus of claim 20 wherein the shield comprises a thin metal film permitting passage of at least soft X rays having an energy of 1 keV and below;
a support film attached to said thin metal film and having good heat conductivity;
and a support for supporting the thin metal film and the support film.

22. The thin film apparatus of claim 21 wherein the thin metal film is made of material of a small atomic number;
wherein the support film is formed of boron nitride;
wherein the support is formed of silicon.

23. A method of analyzing more than one element present in the neighborhood of the surface of a sample, said method comprising the steps of:
applying energy particles to the surface of said sample;
picking up a plurality of electromagnetic waves, emitted by each of the elements present in the neighborhood of said surface as a result of excitation due to said step of applying energy particles, at angles of a range that includes the angles of total reflection of each of said electromagnetic waves from said surface;
reflecting all of the picked up electromagnetic waves at angles such that the intensities of X-rays emitted by the elements are at a similar level; and
subjecting said totally reflected electromagnetic waves to spectroscopy for detection.

24. The method of claim 23, wherein the sample is a biosample.

25. The method of claim 23, wherein the electromagnetic wave is an electron beam accelerated by an electron beam accelerator.

26. The method of claim 23, wherein the electromagnetic wave is generated by a neutral corpuscular beam.

27. A method of analyzing more than one element present in the neighborhood of the surface of a sample, said method comprising the steps of:
allowing a first electromagnetic wave to fall on the surface of said sample at angles of a range that includes the angle of total reflection of that electromagnetic wave from the surface of said sample;
picking up a plurality of second electromagnetic waves, emitted by each of the elements present in the neighborhood of said surface as a result of excitation due to said step of allowing, at angles of a range that includes the angle of total reflection of each of said second electromagnetic waves from said surface;
reflecting all picked up second electromagnetic waves at angles such that the intensities of X-rays emitted by the elements are at a similar level; and
subjecting said totally reflected second electromagnetic waves to spectroscopy for detection.

28. An elemental analyzer comprising:
an excitation source for exciting more than one element present in the neighborhood of the surface of a sample to emit the characteristic X-ray of each element;
means defining a slit for picking up the emitted characteristic X-ray of each element at angles of a range that includes the angle of total reflection of each of said characteristic X-rays from the surface of said sample;
means for causing total reflection of said characteristic X-rays passing through said slit at angles such that the intensity of X-rays emitted by the elements is at a similar level; and
an X-ray detector for detecting the characteristic X-rays reflected from said means for causing total reflection.

29. The elemental analyzer of claim 28 wherein the means for causing total reflection comprises a mirror assembly comprising a plurality of plane mirrors having reflecting surfaces made of different materials.

30. The elemental analyzer of claim 28 wherein the means for causing total reflection comprises a curved mirror having its reflecting surface composed of different materials in different areas.

31. A method of analyzing more than one element present in the neighborhood of the surface of a sample, said method comprising the steps of:
applying first electromagnetic waves to the surface of said sample;
picking up a plurality of second electromagnetic waves, emitted by each of the elements present in the neighborhood of said surface as a result of excitation due to said step of applying, at angles of a range that includes the angle of total reflection of each of said second electromagnetic waves from said surface;
reflecting all picked up second electromagnetic waves at angles such that the intensities of X-rays emitted by the elements are at a similar level;
subjecting said totally reflected second electromagnetic waves to spectroscopy for detection.

32. An elemental analyzer comprising:
- an excitation source for exciting more than one element present in the neighborhood of the surface of a sample to emit the characteristic X-ray of each element;
- means defining a slit for picking up the emitted characteristic X-ray of each element at angles of a range that includes the angle of total reflection of each of said characteristic X-rays from the surface of said sample;
- a mirror having a curvature in two axial directions, constructed and arranged so that the characteristic X-rays passing through the slit are totally reflected and subsequently focused at angles such that the intensities of X-rays emitted by the elements are at a similar level; and
- an X-ray detector for detecting the characteristic X-rays reflected from said mirror.

33. The elemental analyzer of claim 32, wherein the mirror acts as an optical filter and focuses reflected X-rays at a predetermined location, wherein the mirror comprises two cylindrical mirrors having an elliptical cross-section and wherein a location at which elemental excitation occurs so as to cause emission of a characteristic X-ray, is brought into registry with one of the two foci of the ellipsis and the surface of one mirror is made of an appropriately selected material to provide a filtering action whereas the other mirror is positioned perpendicular to the first mirror and focuses incident X-rays to converge at the predetermined location.

34. The elemental analyzer of claim 33, wherein the X-ray source is a synchrotron radiator.

35. The elemental analyzer of claim 32, wherein the mirror has a base and a film formed on the base, wherein the film is made of a layer of gold about 1000 angstroms thick and is evaporated on the base.

36. The elemental analyzer of claim 35, wherein the base is made of silicon dioxide.

37. The elemental analyzer of claim 35, wherein the base is made of silicon carbide.

38. The elemental analyzer of claim 35, wherein materials forming the mirror are varied throughout the surface of the mirror, and wherein the materials are selected such that materials of a lower density are used to reflect X-rays that are picked up at larger angles of total reflection whereas materials of a higher density are used to reflect X-rays that are picked up at smaller angles of total reflection.

* * * * *